United States Patent [19]

Liss et al.

[11] Patent Number: 4,724,835

[45] Date of Patent: Feb. 16, 1988

[54] LASER THERAPEUTIC DEVICE

[75] Inventors: Saul Liss; Bernard S. Liss, both of Glen Rock; Sam Krakower, Elmwood Park; Ilya Feygin, Westfield, all of N.J.

[73] Assignee: Pain Suppression Labs, Inc., Elmwood Park, N.J.

[21] Appl. No.: 889,596

[22] Filed: Jul. 25, 1986

Related U.S. Application Data

[63] Continuation of Ser. No. 586,560, Mar. 6, 1984, abandoned.

[51] Int. Cl.$^4$ .............................................. A61B 17/36
[52] U.S. Cl. .................................. 128/303.1; 372/32; 372/38; 219/121 LA
[58] Field of Search ............... 128/303.1, 395; 372/28, 372/29, 32, 38; 219/121 L, 121 LA, 121 LP, 121 LR, 121 LQ, 121 LU, 121 LV

[56] References Cited

U.S. PATENT DOCUMENTS

| | | | |
|---|---|---|---|
| 3,296,594 | 1/1967 | Heerden | 219/121 LU |
| 3,315,680 | 4/1967 | Silbertrust et al. | |
| 3,364,497 | 1/1968 | MacAdam | 219/121 LQ |
| 3,410,203 | 11/1968 | Fischbeck | 219/121 LP |
| 3,456,651 | 7/1969 | Smart | |
| 3,518,418 | 6/1970 | Dubois | |
| 3,806,829 | 4/1974 | Duston et al. | 219/121 LA |
| 3,818,914 | 6/1974 | Bender | |
| 3,848,970 | 11/1974 | Goodell | 219/121 LR |
| 3,900,034 | 8/1975 | Katz et al. | |
| 3,902,502 | 9/1975 | Liss | |
| 4,232,678 | 11/1980 | Skovajsa | |
| 4,243,951 | 1/1981 | Wolkstein et al. | 372/38 |
| 4,319,203 | 3/1982 | Brosio et al. | 372/30 |
| 4,359,773 | 11/1982 | Swartz et al. | 372/29 |
| 4,385,386 | 5/1983 | Ozeki et al. | 372/29 |
| 4,396,285 | 8/1983 | Presta et al. | |
| 4,468,773 | 8/1984 | Seaton | 372/28 |
| 4,472,807 | 9/1984 | Chubb et al. | 372/38 |

OTHER PUBLICATIONS

"21 & Change", by Alan Gold, The Quarter Racing Record, Feb. 15, 1983.

Primary Examiner—William E. Kamm
Assistant Examiner—Ruth S. Smith
Attorney, Agent, or Firm—Hopgood, Calimafde, Kalil, Blaustein & Judlowe

[57] ABSTRACT

Laser therapeutic apparatus irradiates an area of cutaneous and/or subcutaneous physical injury, with a pulsed laser wave, producing healing and pain reduction. A pulsed laser beam of desired frequency is produced by reducing the output of an oscillator via a frequency multiplier which is varied in accordance with the off-nominal frequency deviation desired, if any. The rate multiplier output wave is divided down to a selected frequency and, after amplification, generates pulsed lasing energy.

In accordance with varying aspects of the instant invention, a plurality of output lasing units, and optical diffusing lenses, are provided for controlled irradiation of an entire injured area. Circuitry is also provided for detecting pulsed infrared light.

7 Claims, 8 Drawing Figures

LASER THERAPEUTIC DEVICE

This application is a continuation of application Ser. No. 586,560, filed Mar. 6, 1984, now abandoned.

BACKGROUND OF THE INVENTION

The present invention relates generally to laser therapeutic devices used to promote healing and reduce pain in injured mammalian tissue and, more particularly, to an improved laser therapeutic device whose performance is enhanced and its ease of operation improved.

In this regard it is important to distinguish between the more commonly known cutting or burning laser used in surgery and therapeutic lasers which promote the healing of injured tissue. In recent years, laser therapeutic devices have come into use to promote the healing of injured tissue, and to reduce pain and edema. Such devices generally use a low power infrared laser in the form of an LED. These devices have been used more often with the treatment of equine injuries. More recently, experimentation has begun with the use of such lasers to treat human injuries. The precise biological mechanism by which these devices operate is unknown. For example, it is not known whether it is the intensity of the photic energy, the rise or fall time of the pulse, or whether it is some other characteristic of the beam. Clinical studies are now under way to gain a better understanding of the biological mechanism.

Laser therapeutic devices generally utilize a separate power supply and a remote probe containing the laser LED. In operation, the user turns on the power, selects a pulse rate in accordance with the particular injury to be treated and thereafter, manually scans the laser beam across the injured tissue for a predetermined period of time. However, such devices are prone to problems because the laser beam must be manually scanned across the injured area. Such manual scanning may result in an inconsistent distribution of laser energy into the wound area. Furthermore, since the device must be manually scanned, the operator is thus required to stand over the patient and manipulate the probe for long periods of time. More recently, in an attempt to avoid the scanning difficulties lasers having a multiplicity of LED's have been proposed. However, these devices simply provide a number of pinpoints rather than uniform energy distribution and cause power supply problems.

SUMMARY OF THE INVENTION

The present invention is directed to a laser therapeutic apparatus which irradiates an area of cutaneous and/or subcutaneous physical injury, with a pulsed laser wave, producing healing and pain reduction. A pulsed laser beam of desired frequency is produced by reducing the output of an oscillator via a frequency multiplier which is varied in accordance with the off-nominal frequency deviation desired, if any. The rate multiplier output wave is divided down to a selected frequency and, after amplification, generates pulsed lasing energy.

In accordance with varying aspects of the instant invention, a plurality of output lasing units, and optical diffusing lenses, are provided for controlled irradiation of an entire injured area. Circuitry is also provided for detecting pulsed infrared light and providing a visual indication thereof.

It is accordingly an object of this invention to provide an improved laser therapeutic device.

It is another object of this invention to provide an improved laser therapeutic device which provides laser energy over a wide area without the need for mechanical scanning.

It is another object of this invention to provide an improved circuitry for a laser therapeutic device.

It is another object of this invention to provide a detector means for infrared pulsed laser energy.

It is another object of this invention to provide an improved laser therapeutic device suitable for treatment of all types of mammalian tissue.

It is another object of this invention to provide an improved laser therapeutic device that may be used by operators of all proficiency levels without the risk of injuring the patient.

It is another object of this invention to provide an improved laser therapeutic device that is particularly suitable for human application.

To these ends, the present invention provides an improved therapeutic laser including means for distributing the laser radiation over a wide area to be treated. The device uses a gallium aluminum arsenide diode as a source of laser energy in the infrared band, at a wavelength of approximately 900 nanometers. Digital circuitry provides the pulse train to activate the diode. Circuitry for detecting pulsed infrared energy is also provided.

BRIEF DESCRIPTION OF THE DRAWINGS

The above and other features and advantages of the present invention will become more clear from the following detailed description of a specific illustrative embodiment thereof presented hereinbelow in conjunction with the accompanying drawing, in which.

DESCRIPTION OF THE PREFERRED EMBODIMENTS

Figure 1:
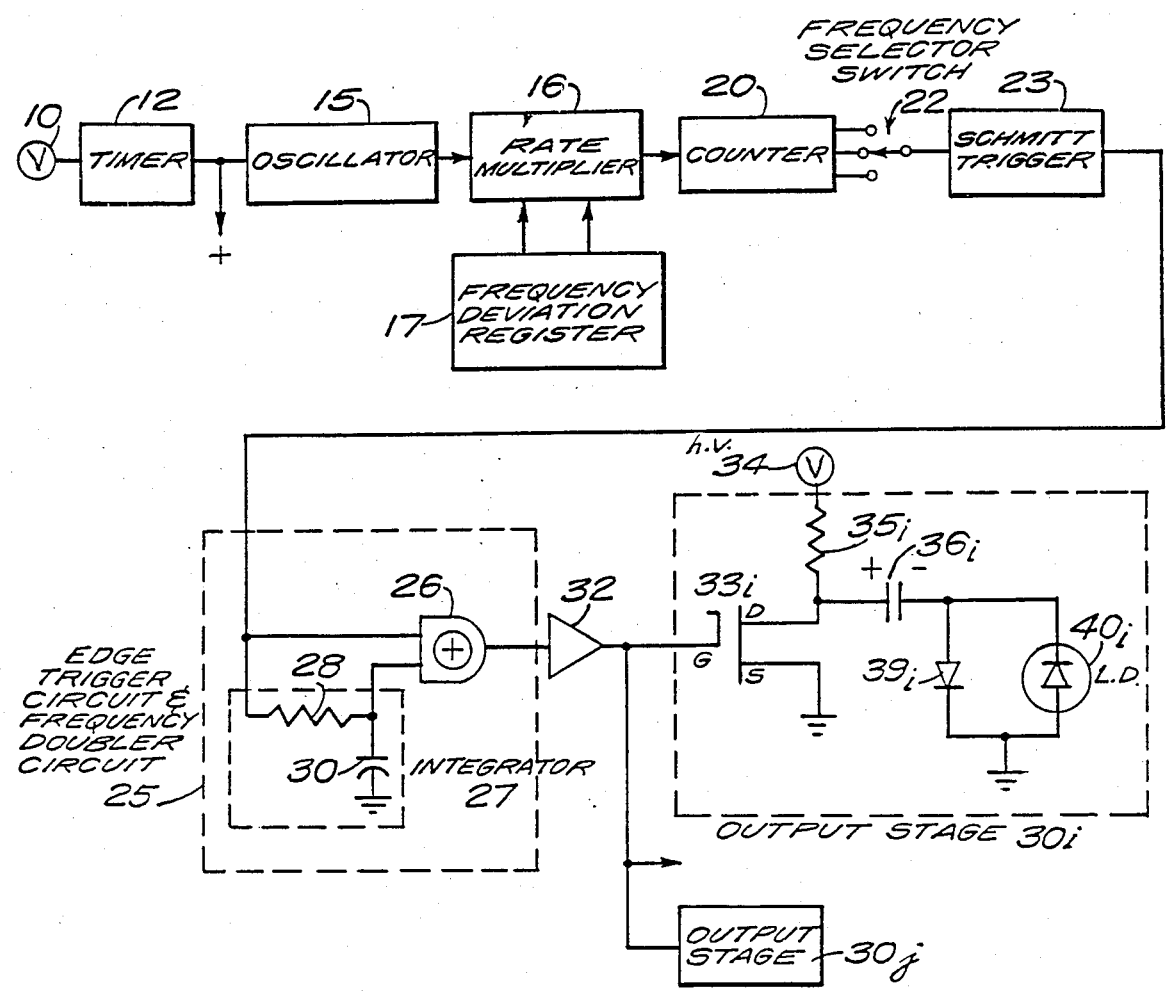
FIG. 1 is a block diagram of electronic apparatus in accordance with the instant invention for producing a therapeutic pulsed laser beam via one or more lasing diodes $40_i$.

Referring to FIG. 1, there is shown pulsed laser generating apparatus which includes an electronic, mechanical, or electromechanical timer 12 for operatively connecting DC potential from a source 10 thereof to the circuitry of the instant invention for a period corresponding to the desired therapeutic period for which pulsed lasing is required. An oscillator 15, enabled during the active period of timer 12 (as is the remaining electronics of FIG. 1) supplies its output wave of periodically recurring pulses to the count input of a rate multiplier 16. Also supplied as inputs to the rate multiplier 16 is a two digit Boolean rate multiplication control variable reposing in frequency deviation register 17.

The stored contents of register 17 operate to vary the output frequency of the rate multiplier 16 in the manner per se well known for digital rate multiplication. Register 17 may comprise an electronic register as shown or, alternatively, an n position mechanical switch for supplying control inputs to rate multiplier 16 dependent upon manual switch setting. As is per se well known, the output frequency $f_{out}$ from rate multiplier 16 equals $$f_{out} = k \cdot f_{in} \cdot D \qquad (1)$$

where k is a proportionality constant typically less than 1, $f_{in}$ is the frequency received from the oscillator 15, and "D" is the rate scaling control variable from register 17. For present therapeutic purposes, it is the function of the rate multiplier 16 to either pass a desired nominal frequency, or to increase or decrease the selected nominal frequency by approximately ±20% depending upon the contents of register 17.

The output frequency of oscillator and rate multiplier 16, possibly deviated by the contents of register 17, are supplied to a binary counter 20 having outputs from plural divider stages supplied as inputs to a selector switch 22. One of the output stages selected by switch 22 is regenerated, i.e. squared in shape, by a Schmitt trigger 23, the output of which is supplied to an edge trigger circuit and frequency doubler circuit 25.

In circuit 25, the regenerated rectangular wave output of Schmitt trigger 23 passes directly to the upper input port of an exclusive OR gate 26 while the same wave is delayed slightly in an integrator 27 (e.g., a series resistor 28 and shunt capacitor 30) before being supplied to a lower input of the exclusive OR gate 26. It will be recalled that the output of an exclusive OR gate assumes its binary "1", high output level when and only when one and only one of its inputs is high. Accordingly, for each output pulse from Schmitt trigger 23, the output of exclusive OR gate 26 goes high and provides a first pulse during the leading edge of the output of Schmitt trigger 23 when the upper input to gate 26 is a "1" but the lower input is a "0" because of the delay engendered by integrator 27; and generates a second output at the trailing edge of the Schmitt trigger output when the upper gate 26 input immediately goes low, whereas the lower input persists at the high or binary "1" level until capacitor 30 can discharge to the binary "0" state. Accordingly, the output of circuit 25 is at twice the frequency as the input supplied thereto.

For purposes of the instant invention, we have found that each of the output lasers $40_i$ should pulse at frequencies of 76, 152 or 304 pulses per second (nominal with possible plus or minus 20% adjustments). These frequencies bear a 2:1 and 4:1 relation with one another, and thus may utilize three consecutive cascaded outputs of the counter 20. Oscillator 15 then runs at a frequency higher than 152 hz (304 hz divided by two for the frequency doubling of circuit 25 decreased by the proportionality "k" factor of rate multiplier 16).

The output pulses from frequency doubler 25 are amplified in amplifier 32 and supplied to one or more output stages $30_i$. One such stage $30_i$ is shown in detail and is representative of the other such stages employed. Each output stage $30_i$ includes a field effect transistor switch $33_i$ having a high voltage source 34 connected by the FET $33_i$ drain-source path to ground via a resistor $35_i$. During the dormant period when the diode laser $40_i$ is off (corresponding to a low output potential from the exclusive OR gate 26 and amplifier 32), high voltage from the source 34 charges a capacitor $36_i$ via a path comprising the resistor $35_i$ and a diode $39_i$. During each pulse period when the output of the gate 26 goes high, amplifier 32 activates the FET switch $33_i$ causing the energy previously stored in the charged capacitor $36_i$ to discharge via the FET drain-source path through the laser diode $40_i$. Accordingly, a pulse of laser energy is emitted for the duration of each output pulse from the exclusive OR gate 26. The lasers $40_i$ in each other output stage $30_i$, if any, similarly emit energy each time the output of exclusive OR gate 26 attains its binary "1" state. A suitable diode $40_i$ is a gallium aluminum arsenide diode operating in the infrared spectrum at approximately 900 nanometers. The pulsed laser output energy operates as above noted to provide its salutary cutaneous and sub-cutaneous healing and pain reducing benefits.

In accordance with one aspect of the instant invention, it is desirable to provide users with a continuous indication within the visible light spectrum to indicate when the output lasers are active. A continuous visible indication is needed because (i) the pulsed energy may be too rapid or too short to be discerned, (ii) the laser devices $40_i$ selected may not emit energy in the visible spectrum, and (iii) where a wide angle dispersion of the beam is provided the energy per unit area is low and thus difficult to detect by conventional means. The detector/active state indicating circuitry of FIG. 2 basically comprises an AC input stage coupled inverting mode operational amplifier 50 coupled via an amplitude signal demodulating detector diode 60 and resistor-capacitor time constant circuit 62-63 to a non-inverting amplifier 66. Connected to the output of the non-inverting amplifier 66 is a visible light spectrum emitting diode (LED) 68 which is illuminated when the FIG. 2 apparatus detects pulsed output light from one or more lasers $40_i$. Also connected to the output of non-inverting amplifier 66 via a scaling network 69-70 is a microammeter 72 which provides an indication of the amplitude or strength of the detected pulsed laser signal.

In the absence of any incident pulsed laser energy, the output of the inverting amplifier 50 attains a low output level responsive to the absence of input drive via capacitor 54. Thus little or no input is supplied to the non-inverting amplifier 66. When this condition persists, the corresponding low output of the non-inverting operational amplifier 66 does not energize, i.e., does not turn on light emitting diode 68 and does not supply a meaningful signal via microammeter 72.

In the presence of pulsed energy, the incoming laser pulses alternately turn a laser spectrum responsive transducer (e.g., a photocell or silicon photodiode) on and off. With the diode on, a capacitor 56 charges through resistor 58. The ensuing change in potential across capacitor 56 as the transducer 55 alternately is rendered conductive and non-conductive is coupled by capacitor 54 to the inverting input terminal of the operational amplifier 52. The operational amplifier 52 operates in an inverting mode such that its output produces large, inverted replicas of the incident laser energy pulses. As is per se well known, the sensitivity of amplifier 52 is adjusted via the setting of a potentiometer 76.

In the presence of the pulsed laser energy, the voltage at the output of the operational amplifier 52 is detected via the diode 60 and the shunt resistor capacitor 63 and 62 which operate as a peak detector or output signal demodulator. The resulting positive signal persisting across capacitor 62 is supplied to the non-inverting input of the operational amplifier 66 which thus provides a direct current output potential proportional to the peak detected potential reposing across capacitor 62 and resistor 63 with a gain determined by the ratio of resistors 67 and 65. Thus, the output of operational amplifier 66 is high in the presence of detected pulsed laser energy to activate the light emitting diode 68 and the microammeter 72, and is low to disable these active state indicators in the absence of any detected pulsed laser energy.

Figure 2:
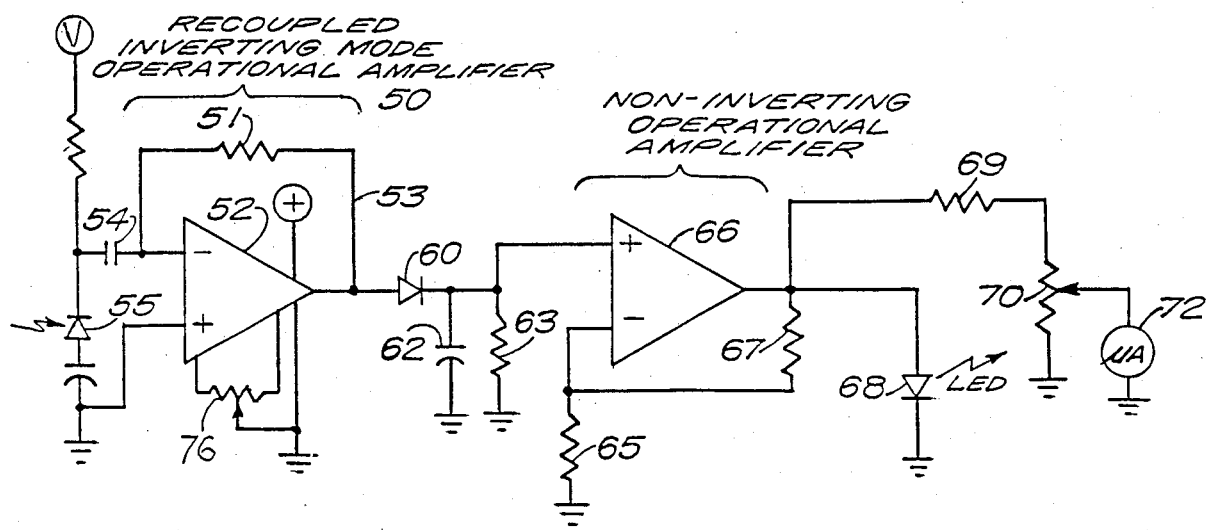
FIG. 2 is a schematic diagram depicting indicator apparatus selectively responsive to incident pulsed laser energy for providing a constant visible light spectrum "active state" indication via a light emitting diode 68.

The circuitry of FIGS. 1 and 2 has thus been shown to generate the requisite pulsed laser energy with the frequency deviation control desired; and to provide an output indication via LED 68 of an active state for the laser while providing analog measure of the strength of the laser pulses at the microammeter 72.

Figure 3A:
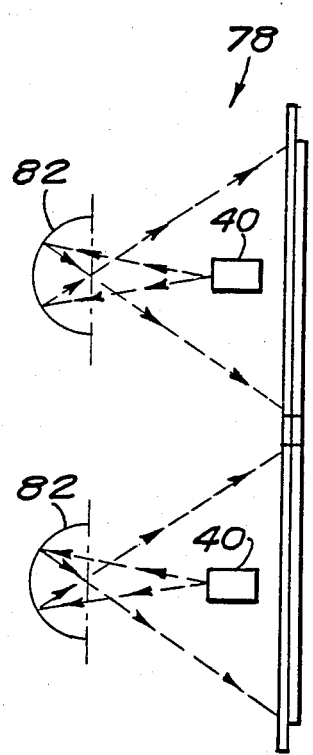
*FIGS. 3 through 5 depict mechanical implementations for the electronic apparatus of FIGS. 1 and 2 which employ plural operative lasing diodes $40_i$.
*Includes FIGS. 3a, 3b, 3c, 4, 5a and 5b.
Figure 3B:
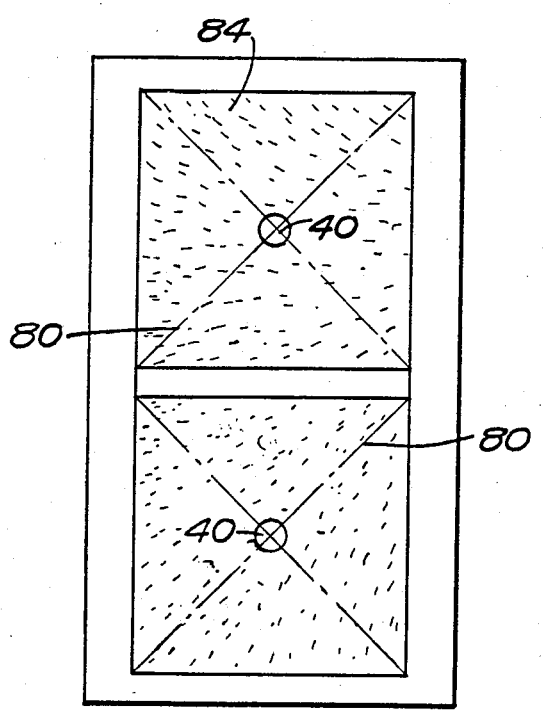

In accordance with another aspect of the invention, FIG. 3 illustrates a first embodiment of a head assembly for providing a uniform wide-angle energy distribution of the radiant energy output of lasing diodes $40_i$. FIG. 3a and 3b illustrate a wide angle head assembly 78 in which two lasing diodes $40_i$ are mounted to X-shaped cross-braces 80 so that the head of each diode $40_i$ faces rearwardly and is aimed at concave curved mirrors 82 which reflect the light back towards diodes 40 in a wide arc. Mounted in front of diode $40_i$ is a light diffusing or dispersing lens element 84 to further uniformly distribute the infrared energy. While known light diffusing elements such as ground or frosted glass may be used for lens element 84, a diffusion lens causes light attenuation. Obviously, attenuation is not desirable. Thus, rather than a diffusion element, a light dispersion element utilizing clear glass or plastic having a microprismatic structure is preferable. Each of the microprisms act to further reflect and refract the light and thus optimizes energy distribution.

Figure 3C:
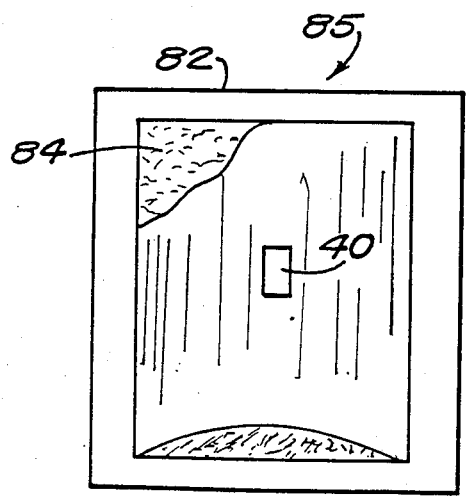

If a more compact head assembly is desired, FIG. 3c illustrates such an arrangement of a head assembly 85. Assembly 85 has the lasing diode $40_i$ mounted vertically generally at the focal point of curved reflector 82. Dispersing element 84 is disposed in front of diode $40_i$ and reflector 82 to provide further distribution of the radiant energy. In this arrangement diode $40_i$ emits light both toward reflector 82 and forwardly to provide a wide angle blend of direct and reflected energy. This construction provides a compact arrangement of the head assembly and two assemblies may again be used in side by side array.

In these constructions each diode and reflector assembly provides uniform energy distribution over an area of approximately one inch by one inch or a total of two square inches for both diode assemblies. This size head has been found optimum for a wide variety of applications. Should a larger area be needed, additional diode assemblies may be added.

Figure 4:
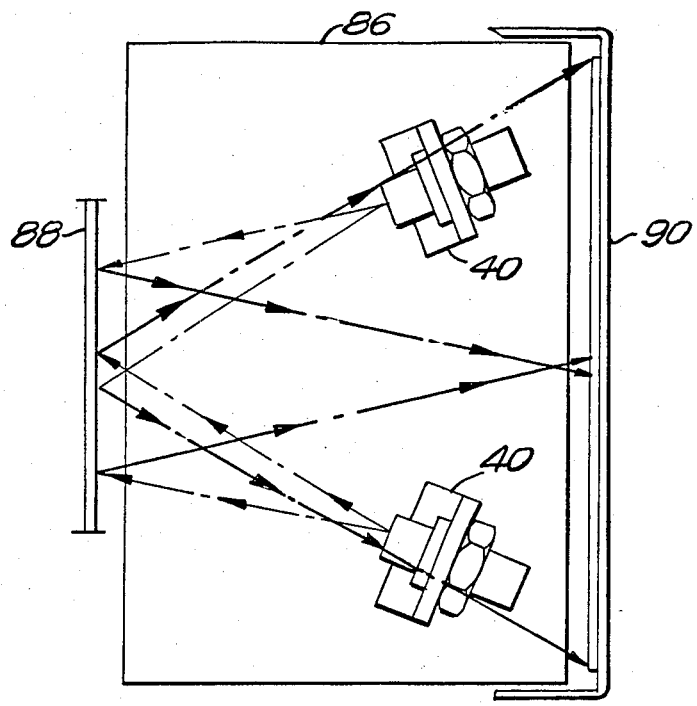

FIG. 4 illustrates another embodiment of a wide angle laser head assembly utilizing a single flat mirror rather than two curved mirrors. In this embodiment, lasing diodes $40_i$ are angled rearwardly at each side of a head assembly 86. Diodes $40_i$ are each aimed at a flat mirror surface 88. The laser light is then reflected back towards a forwardly mounted light dispersing element 90, similar to that described above with respect to FIG. 3. This arrangement has an advantage in that the laser diodes $40_i$ are not centrally located with respect to dispersion element 90 and, thus, do not block the light at the center. It has been found that a suitable mounting angle for the laser diodes is at an angle of 20° from the perpendicular to dispersion element 90. Of course, other suitable angles may be used, depending on the size and overall dimensions of head assembly 86. Dispersion element 92 in this construction is approximately one inch by two inches.

Figure 5A:
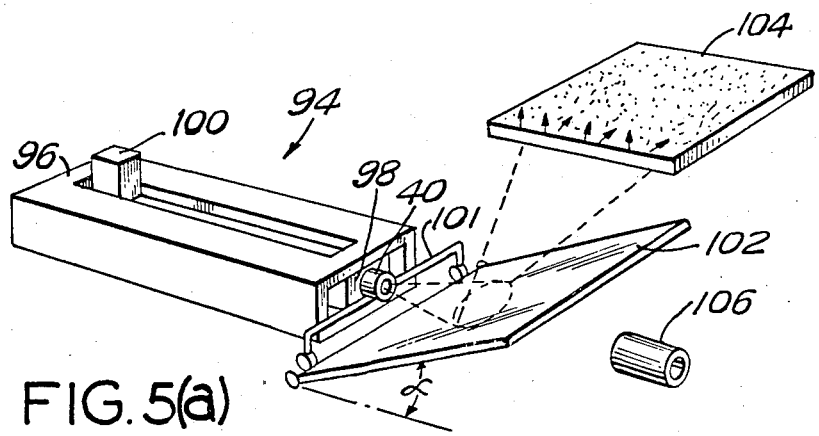

In certain types of treatment, a non-dispersed narrowly directed beam of a single laser diode may be appropriate. Accordingly, a laser head which provides either a narrow angle beam or a wide angle beam is desirable. This may be accomplished by adding a separate switchable non-dispersed diode to any of the above described wide angle assemblies. However, in order to reduce the cost of production of a dual angle head, it is desirable that the same laser diode be used to provide either a wide angle or a concentrated beam. The head assembly 94 illustrated in FIGS. 5a and 5b provides such an arrangement and further includes a mechanical shutter for the diode which is required under certain governmental regulations.

Head assembly 94 includes a slide switch 96 having three positions which correspond to a wide angle beam, a narrow beam and a shuttered position. Lasing diode $40_i$ is mounted to a sliding carrier 98 which is moved by a manually operated toggle 100, as toggle 100 moves forward, lasing diode $40_i$ will move forward. The forward portion of carrier 98 includes a mirror deflector 101 which engages a spring loaded pivoting mirror 102. When toggle 100 is in its rearmost first position as shown in FIG. 5a, mirror deflector 101 will be located rearwardly with respect to mirror 102 and will thus permit it to assume an angle $\alpha$. In this position, the light from diode $40_i$ will be reflected from mirror 102 towards a dispersing lens element 104 similar to those previously described. In this position, mirror 102 and dispersing element 104 will provide a wide angle uniform distribution of infrared radiant energy.

Figure 5B:
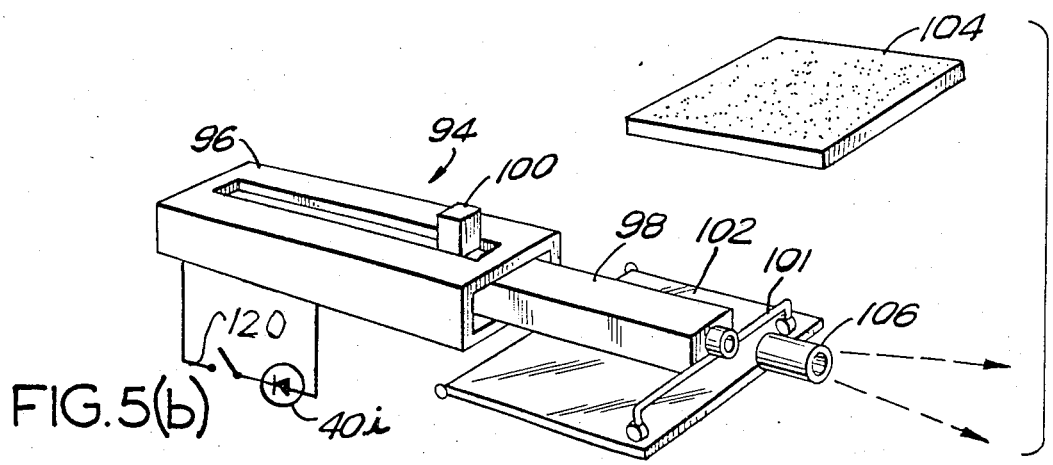

When the toggle 100 is moved all the way forward into its second position as shown in FIG. 5b, mirror deflector 101 will act to pivot mirror 102 downwardly out of the path of lasing diode $40_i$. Thus, the output of diode $40_i$ will not be reflected towards dispersion element 104, but rather will impinge on a snout lens 106 which will provide a relatively narrow beam.

When toggle 100 is moved to a neutral position, between the first and second positions, the mirror will pivot to an angle between $\alpha$ and 0 and the output of diode $40_i$ will impinge on neither dispersion element 104 nor snout lens 106. Thus, the mirror acts as a mechanical shutter to block the escape of radiant energy. Furthermore, in its neutral position, toggle 100 is arranged to electrically disconnect diode $40_i$ by a switch 120 as shown in FIG. 5b so that both electrical and mechanical closure of the beam is provided.

The above-described arrangement is merely illustrative of the principles of the present invention. Numerous modifications and adaptations thereof will be readily apparent to those skilled in the art without departing from the spirit and scope of the present invention.

What is claimed is:

1. A circuit for operating a laser therapeutic device comprising:
   a power source;
   an oscillator connected to said power source for providing an output of a predetermined frequency;
   a rate multiplier having a count input connected to the output of said oscillator, said rate multiplier having a second input for receiving a rate multiplication control variable and an output, the frequency of the output of said rate multiplier being a function of the rate multiplication control variable received;

a frequency deviation register coupled to said second input of said rate multiplier, said register supplying said rate multiplication control variable to control the frequency output of said rate multiplier;

a binary counter having an input connected to the output of said rate multiplier and an output;

a regenerating circuit having an input connected to the output of said binary counter and output means for providing a regenerated rectangular pulse train; and an output stage including an infrared laser diode, said output stage having an input connected to the output of said regenerating circuit to receive the pulse train generated by said regenerating circuit to activate said diode upon the receipt of each pulse.

2. The circuit as claimed in claim 1, wherein said regenerating circuit comprises a Schmitt trigger.

3. The circuit as claimed in claim 1, wherein said binary counter includes multiple divider stages and means for selecting one of said multiple stages.

4. The circuit as claimed in claim 1, wherein said output stage includes an electronic switch having a power input connected to a power source, a control input and an output connected to said laser diode, the control input of said electronic switch receiving said pulse train from said regenerating circuit.

5. The circuit as claimed in claim 4, wherein said electronic switch comprises a field effect transistor.

6. The circuit as claimed in claim 1, further including a frequency doubling circuit disposed between said regenerating circuit and said output stage.

7. The circuit as claimed in claim 6, wherein said frequency doubling circuit comprises an exclusive OR gate having a first input connected to said output of said regenerating circuit and a second input connected to the output of said regenerating circuit through an integrating circuit to delay in time the arrival of the pulse train to said second input and thereby double the output of said frequency doubler circuit.

* * * * *